US012594238B2

(12) United States Patent
Spadaro et al.

(10) Patent No.: US 12,594,238 B2
(45) **Date of Patent: *Apr. 7, 2026**

(54) LOW HYGROSCOPICITY ACTIVE POWDER COMPOSITIONS

(71) Applicant: PHILIP MORRIS PRODUCTS S.A., Neuchâtel (CH)

(72) Inventors: Fabiana Spadaro, Lausanne (CH); Gérard Zuber, Boulens (CH)

(73) Assignee: Philip Morris Products S.A., Neuchâtel (CH)

( * ) Notice: Subject to any disclaimer, the term of this patent is extended or adjusted under 35 U.S.C. 154(b) by 386 days.

This patent is subject to a terminal disclaimer.

(21) Appl. No.: 18/022,638

(22) PCT Filed: Aug. 31, 2021

(86) PCT No.: PCT/IB2021/057952
§ 371 (c)(1),
(2) Date: Feb. 22, 2023

(87) PCT Pub. No.: WO2022/049487
PCT Pub. Date: Mar. 10, 2022

(65) Prior Publication Data

US 2023/0310315 A1 Oct. 5, 2023

(30) Foreign Application Priority Data

Sep. 3, 2020 (EP) .................................... 20194434

(51) Int. Cl.
*A61K 9/00* (2006.01)
*A61K 9/16* (2006.01)
*A61K 31/444* (2006.01)

(52) U.S. Cl.
CPC .......... *A61K 9/0075* (2013.01); *A61K 9/1623* (2013.01); *A61K 31/444* (2013.01)

(58) Field of Classification Search
CPC ... A61K 9/0075; A61K 9/1623; A61K 31/444
See application file for complete search history.

(56) References Cited

U.S. PATENT DOCUMENTS 8,207,346 B2 6/2012 Puthiaparampil et al.
8,557,999 B2 10/2013 Puthiaparampil et al.
(Continued)

FOREIGN PATENT DOCUMENTS

RU 2697862 C2 8/2019
WO WO 2011/119722 A2 9/2011
(Continued)

OTHER PUBLICATIONS

Chen et al., "Amorphous powders for inhalation drug delivery", Advanced Drug Delivery Reviews 100 (2016) 102-115. (Year: 2016).*
(Continued)

*Primary Examiner* — Jianfeng Song
(74) *Attorney, Agent, or Firm* — Mueting Raasch Group

(57) ABSTRACT

An inhalable powder includes crystalline dry powder particles. The crystalline dry powder particles include a solid salt of an alkaloid and a sugar alcohol. The salt is solid at 25° C. The sugar alcohol may include mannitol, erythritol, myo-inositol, adonitol, xylitol, or a combination thereof. The inhalable powder may be part of a powder system that further includes a second population of particles having a particle size greater than that of the crystalline dry powder particles.

18 Claims, 5 Drawing Sheets

(56) References Cited

U.S. PATENT DOCUMENTS

| | | | | |
|---|---|---|---|---|
| 9,387,201 | B2 | 7/2016 | Williams | |
| 2003/0129140 | A1* | 7/2003 | Tarara | A61P 11/00 514/35 |
| 2004/0002520 | A1 | 1/2004 | Soderlund et al. | |
| 2012/0042886 | A1 | 2/2012 | Piskorz | |
| 2012/0135969 | A1* | 5/2012 | Weiler | A61P 11/06 514/169 |
| 2013/0298921 | A1 | 11/2013 | Williams | |
| 2017/0172996 | A1 | 6/2017 | Stenzler et al. | |
| 2018/0318170 | A1 | 11/2018 | Bosch et al. | |
| 2019/0133940 | A1 | 5/2019 | Zuber et al. | |

FOREIGN PATENT DOCUMENTS

| | | | | |
|---|---|---|---|---|
| WO | WO-2011159633 | A1 * | 12/2011 | A61K 31/427 |
| WO | WO 2013/032558 | A2 | 3/2013 | |
| WO | WO 2015/173648 | A2 | 11/2015 | |
| WO | WO 2017/048974 | A1 | 3/2017 | |
| WO | WO 2017/109625 | A1 | 6/2017 | |
| WO | WO 2017109626 | A1 | 6/2017 | |
| WO | WO 2017/212249 | A1 | 12/2017 | |
| WO | WO 2018/002756 | A1 | 1/2018 | |
| WO | WO 2018/002779 | A1 | 1/2018 | |
| WO | WO 2018/163085 | A1 | 9/2018 | |
| WO | WO-2019003118 | A1 * | 1/2019 | A61M 15/0035 |
| WO | WO 2020/023614 | A1 | 1/2020 | |
| WO | WO 2020/127225 | A1 | 6/2020 | |

OTHER PUBLICATIONS

Ayers et al., "A general procedure for the enantioselective synthesis of the minor Tobacco alkaloids nornicotine, anabasine, and anatabine," *The AAPS Journal*, Sep. 2005;7(3): Article 75; E752-E758.

Dixit et al., "Spray Drying: A Crystallization Technique: A Review," *Intl J of Drug Form & Research*, Oct.-Nov. 2010; 1(II):1-29.

Marple et al., "Next Generation Pharmaceutical Impactor (A new Impactor for Pharmaceutical Inhaler Testing). Part I: Design," *Journal of Aerosol Medicine*, 2003;16(3); 283-299.

Marple et al., "Next Generation Pharmaceutical Impactor (A new Impactor for Pharmaceutical Inhaler Testing). Part II: Archival Calibration," Journal of Aerosol Medicine, 2003;16(3); 301-324.

European Search Report for EP 20194434.5 issued by the European Patent Office dated Mar. 11, 2021; 8 pgs.

International Search Report and Written opinion for PCT/IB2021/057952, issued by the European Patent Office on Nov. 19, 2021; 13 pgs.

International Preliminary Report on Patentability for PCT/IB2021/057952, issued by the European Patent Office on Sep. 19, 2022; 15 pgs.

Kaialy and Nokhodchi, "Freeze-Dried Mannitol for Superior Pulmonary Drug Delivery via Dry Powder Inhaler," *Pharm Res*, 2013;30;458-477.

Russian Office Action for RU 2023107778 issued by the Russian Patent Office on 4 Feb. 4, 2025; 19 pgs. including English translation.

* cited by examiner

LOW HYGROSCOPICITY ACTIVE POWDER COMPOSITIONS

This application is the § 371 U.S. National Stage of International Application No. PCT/IB2021/057952, filed 31 Aug. 2021, which claims the benefit of European Application No. 20194434.5, filed 3 Sep. 2020, the disclosures of which are incorporated herein by reference.

The present disclosure relates to active powder compositions that exhibit low hygroscopicity. Sugar or sugar alcohol and an active agent form crystalline dry particles.

Active powder compositions have been described having an amorphous structure. An amorphous structure lacks long range order characteristics of a crystalline form. These amorphous powder compositions generally exhibit a greater water solubility than crystalline counterpart powder compositions and may exhibit a reduced shelf life or delivery due to ambient moisture absorption.

Amorphous powder compositions tend to be hygroscopic and agglomerate, become sticky, or even liquify when exposed to humid conditions, for example, a relative humidity at or above about 40% and temperatures at or above about 25° C. Tropical conditions, for example, a relative humidity at or above about 60% and temperatures at or above about 30° C. may exacerbate these problems. Transport and storage of these amorphous powder compositions may require hermetic packaging to maintain the stability of the amorphous powder compositions. Once the hermetic seal has been compromised (for example, package has been opened by a consumer), the contents may rapidly absorb humidity. In addition, delivery of amorphous powder compositions to the lungs of the consumer may require separation of humidity from the inhalation airflow, resulting in increased complexity and cost of the associated inhaler device or article.

It would be desirable to provide an active powder composition that exhibits a lowered hygroscopicity. It would be desirable to provide an active powder composition that resists water or humidity absorption when exposed to humid or tropical conditions. It would be desirable to provide an active powder composition that exhibits a reduced agglomeration when exposed to humid or tropical conditions. It would be desirable to provide an active powder composition that is stable and possesses a long shelf life.

According to an aspect of the present invention, there is provided an inhalable powder composition including crystalline dry powder particles. The crystalline dry powder particles include sugar or a sugar alcohol and an active agent. Preferably the crystalline dry powder particles are dry powder particles that include a sugar alcohol and a solid salt of an alkaloid.

Advantageously, the inhalable powder exhibits a low or reduced hygroscopicity. The inhalable powder does not readily absorb water or moisture when exposed to humid or tropical conditions. The inhalable powder does not readily agglomerate when exposed to humid or tropical conditions. Further advantageously, the inhalable powder is stable and possesses a long shelf life.

The phrase "spray drying temperature" refers to a temperature of the liquid mixture exiting the nozzle of the spray dryer. The spray drying temperature may preferably be less than about 80 degrees Celsius, or less than 70 degrees Celsius, or less than 65 degrees Celsius, or less than 60 degrees Celsius, or less than 55 degrees Celsius.

The term "crystalline" refers to a solid form of a compound exhibiting long range order in a microscopic lattice. A skilled person can identify a crystalline material by inspection of an X-ray diffraction (XRD) pattern of that material, such as a powder X-ray diffraction (pXRD) trace. For example, crystalline XRD patterns are illustrated in FIG. 1 and FIGS. 4-8 herein. A crystalline material may exhibit some amorphous structure.

The phrase "crystalline dry powder particles" refers to a free-flowing particle composition that has crystalline material.

The term "active agent" refers to an alkaloid or other pharmaceutically active ingredient. The "active agent" always refers to just the active agent component of a compound. Preferably the active agent may be a salt of the active agent.

The term "low hygroscopicity" refers to a measured hygroscopicity value of a water uptake of 5% wt or less, or 4% or less, or 3% or less, or 2.5% or less, or 2% or less. Hygroscopicity may be determined by measuring the water uptake or absorption (wt % increase) of the sample when exposed to tropical conditions (75% relative humidity and 30 degrees Celsius atmosphere) for a 20-minute time duration. Prior to exposure to tropical conditions, the sample is equilibrated at 0% relative humidity, and 25 degrees Celsius atmosphere for 24 hours to reduce or remove non-bonded water from the sample. The hygroscopicity value may be measured utilizing a "Vapor Sorption Analyzer SPSx-1u High Load" manufactured by ProUmid GmbH & Co. KG, as described in the Examples below.

A method of forming the crystalline dry powder particles may include mixing the active agent with the sugar or sugar alcohol and the liquid carrier, where the active agent is added in a solid form. In some embodiments, the active agent is a base and is mixed with an acid to form a salt. For example, the active agent may comprise an alkaloid such as nicotine, anatabine, or anabasine provided as a free base and combined with an acid to form a pharmaceutically acceptable salt.

Any pharmaceutically acceptable salt may be used to form the salt of the active agent. In a preferred embodiment, the salt of the alkaloid may be solid at room temperature (for example, solid at 25° C.). Suitable salts include, for example, a salt of aspartic acid ("aspartate"), gentisic acid ("gentisate"), benzoic acid ("benzoate"), lactic acid ("lactate"), malic acid ("malate"), fumaric acid ("fumarate"), maleic acid ("maleate"), muconic acid ("muconate"), hydrochloric acid ("hydrochlorate"), alfa-resorcylic acid ("alfa-resorcylate"), beta-resorcylic acid ("beta-resorcylate"), oxalic acid ("oxalate"), p-anisic acid ("anisate"), tartaric acid ("bitartrate"), or glutaric acid ("glutarate"). Preferably the salt comprises aspartate, bitartrate, malate, or glutarate.

A preferred alkaloid is nicotine. Nicotine may preferably be a nicotine salt. Nicotine salts include, for example, nicotine aspartate, nicotine bitartrate, nicotine glutarate, nicotine lactate, nicotine gentisate, nicotine benzoate, nicotine fumarate, nicotine hydrochlorate, nicotine alfa-resorcylate, nicotine beta-resorcylate, nicotine oxalate, nicotine malate, and nicotine anisate. A preferred nicotine salt is selected from one or more of nicotine bitartrate, nicotine aspartate, nicotine malate, and nicotine glutarate.

Another preferred alkaloid is anatabine. Anatabine may preferably be an anatabine salt. A preferred anatabine salt is anatabine glutarate. Anatabine glutarate is described, for example, in WO2020/127225A1.

Anatabine is an alkaloid present in tobacco and, in lower concentrations, in a variety of foods, including green tomatoes, green potatoes, ripe red peppers, tomatillos, and sun-dried tomatoes. It is a main active component of the marketed dietary supplement anatabloc providing anti-inflammatory support, as disclosed in U.S. Pat. No. 9,387,201 and WO 2013/032558. The preparation of isolated forms of anatabine is described in WO 2011/119722, for example.

Anatabine is also known as 3-(1,2,3,6-tetrahydropyridin-2-yl)pyridine. Enantioselective syntheses of S- and R-enantiomers of anatabine are described, for example, in Ayers, J. T.; Xu, R.; Dwoskin, L. P.; Crooks, P. A. A general procedure for the enantioselective synthesis of the minor Tobacco alkaloids nornicotine, anabasine, and anatabine. The AAPS Journal 2005; 7(3) Article 75.

The term "anatabine" as used here may refer to (1) a racemic mixture of anatabine (R,S); (2) a purified form of S-(−)-anatabine; or (3) a purified form of R-(+)-anatabine. A preferred anatabine compound is anatabine salt such as anatabine glutarate or 3-(1,2,3,6-tetrahydropyridin-2-yl) pyridine glutarate. Preferably, the 3-(1,2,3,6-tetrahydropyridin-2-yl)pyridine glutarate has a 1:1 molar ratio of 3-(1,2,3,6-tetrahydropyridin-2-yl)pyridine to glutarate.

Pharmaceutically acceptable salts of anatabine are described in U.S. Pat. Nos. 8,207,346 and 8,557,999. In particular, Example 6 of U.S. Pat. No. 8,207,346 and Example 6 of U.S. Pat. No. 8,557,999 describe the preparation of anatabine tartrate and anatabine citrate by addition of tartaric acid or citric acid to a solution of anatabine in acetone.

It is to be understood that any reference to "3-(1,2,3,6-tetrahydropyridin-2-yl)pyridine glutarate" or "anatabine glutarate" herein is to be understood as also referring to any pharmaceutically acceptable solvate thereof.

The 3-(1,2,3,6-tetrahydropyridin-2-yl)pyridine glutarate has a chemical structure represented by the following formula (I):

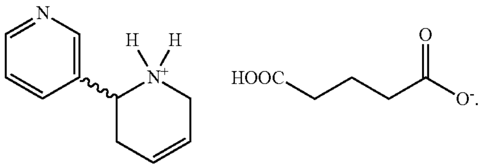

In a preferred embodiment, the 3-[1,2,3,6-tetrahydropyridin-2-yl]pyridine glutarate may thus have the following formula (Ia):

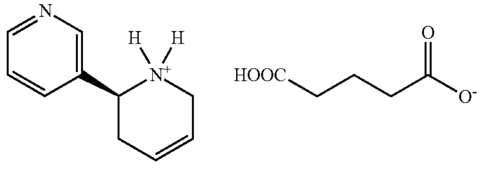 [SMILES: C1=CC[C@@H](c2cccnc2)[NH2+]C1 ; O=C([O-])CCCC(=O)O]

Preferably the anatabine glutarate is a specific polymorph (herein also referred to as polymorphic form) of the 3-(1,2,3,6-tetrahydropyridin-2-yl)pyridine glutarate and in particular of the crystal of the 3-(1,2,3,6-tetrahydropyridin-2-yl) pyridine glutarate. The polymorph preferably has an X-ray powder diffraction pattern (CuKα) substantially as shown in FIG. 1. The polymorph preferably has an X-ray powder diffraction pattern (CuKα) comprising one or more peaks selected from 8.0±0.2°2θ, 11.0±0.2°2θ, 13.3±0.2°2θ, 16.5±0.2°2θ, 18.0±0.2°2θ, 20.7±0.2°2θ, 21.0±0.2°2θ, 21.4±0.2°2θ, 22.0±0.2°2θ, 22.3±0.2°2θ, 23.3±0.2°2θ and 24.5±0.2°2θ. More preferably, the polymorph preferably has an X-ray powder diffraction pattern (CuKα) comprising one or more peaks selected from 8.0±0.2°2θ, 13.3±0.2°2θ, 16.5±0.2°2θ, 21.4±0.2°2θ, 22.0±0.2°2θ and 24.5±0.2°2θ.

Still more preferably, the polymorph preferably has an X-ray powder diffraction pattern (CuKα) comprising one or more peaks selected from 8.0±0.1 °2θ, 11.0±0.1 °2θ, 13.3±0.1 °2θ, 16.5±0.1 °2θ, 18.0±0.1 °2θ, 20.7±0.1 °2θ, 21.0±0.1 °2θ, 21.4±0.1 °2θ, 22.0±0.1 °2θ, 22.3±0.1 °2θ, 23.3±0.1 °2θ and 24.5±0.1 °2θ. Even more preferably, the polymorph preferably has an X-ray powder diffraction pattern (CuKα) comprising one or more peaks selected from 8.0±0.1 °2θ, 13.3±0.1 °2θ, 16.5±0.1 °2θ, 21.4±0.1 °2θ, 22.0±0.1 °2θ and 24.5±0.1 °2θ.

Even more specifically, the polymorph preferably has an X-ray powder diffraction pattern (CuKα) comprising one or more peaks selected from 7.960±0.2°2θ, 10.907±0.2°2θ, 13.291±0.2°2θ, 14.413±0.2°2θ, 15.239±0.2°2θ, 16.479±0.2°2θ, 17.933±0.2°2θ, 20.610±0.2°2θ, 20.977±0.2°2θ, 21.318±0.2°2θ, 21.927±0.2°2θ, 22.203±0.2°2θ, 22.792±0.2°2θ, 23.246±0.2°2θ, 24.426±0.2°2θ and 24.769±0.2°2θ. Still more specifically, the polymorph preferably has an X-ray powder diffraction pattern (CuKα) comprising one or more peaks selected from 7.960±0.1 °2θ, 10.907±0.1 °2θ, 13.291±0.1 °2θ, 14.413±0.1 °2θ, 15.239±0.1 °2θ, 16.479±0.1 °2θ, 17.933±0.1 °2θ, 20.610±0.1 °2θ, 20.977±0.1 °2θ, 21.318±0.1 °2θ, 21.927±0.1 °2θ, 22.203±0.1 °2θ, 22.792±0.1 °2θ, 23.246±0.1 °2θ, 24.426±0.1 °2θ and 24.769±0.1 °2θ. The above form of anatabine glutarate may be prepared using a method comprising the steps of:

a) preparing a solution comprising 3-[1,2,3,6-tetrahydropyridin-2-yl]pyridine, glutaric acid and a solvent,
b) allowing the formation of a salt of 3-[1,2,3,6-tetrahydropyridin-2-yl]pyridine with the glutaric acid, and
c) recovering the 3-[1,2,3,6-tetrahydropyridin-2-yl]pyridine glutaric acid salt.

The solvent used in the preparation of the solution of 3-[1,2,3,6-tetrahydropyridin-2-yl]pyridine, glutaric acid and a solvent preferably comprises 2-methyltetrahydrofuran, acetonitrile and/or ethyl acetate. More preferably, the solvent comprises 2-methyltetrahydrofuran.

The method may furthermore comprise a step of d) recrystallizing the 3-[1,2,3,6-tetrahydropyridin-2-yl]pyridine glutaric acid salt. Suitable solvents for this recrystallization include acetonitrile.

In step a), the anatabine glutarate can be prepared by combining anatabine free base, a solvent, and glutaric acid to create a reaction mixture. Anatabine glutarate typically forms in such a reaction mixture through contact of anatabine free base with glutaric acid. Preferably, anatabine free base as a 1 to 5 mass-% solution in acetonitrile is combined with glutaric acid.

Preferably a solution or suspension of anatabine free base, a solvent and glutaric acid is combined to form a reaction mixture, followed by precipitation and recovery of the anatabine glutarate salt from the mixture. Glutaric acid may be added either as a solid or as a solution or a suspension in a solvent.

The solvent is preferably selected from the group consisting of alkanols containing 1 to 8 carbon atoms, aliphatic esters containing 3 to 8 carbon atoms, aliphatic linear or cyclic ethers containing 3 to 8 carbon atoms, aliphatic ketones containing 3 to 8 carbon atoms, $C_{6-12}$ aromatic hydrocarbons (such as benzene and napthalene), acetonitrile, water, and any mixtures thereof. Preferably, the solvent is selected from aliphatic esters containing 3 to 8 carbon atoms, aliphatic cyclic ethers containing 3 to 8 carbon atoms, acetonitrile and a mixture thereof. More preferably, the solvent is selected from ethyl acetate, acetonitrile, 2-methyltetrahydrofuran, and any mixtures thereof. Even more preferably, the solvent contains acetonitrile. Still more preferably, the solvent is acetonitrile.

The anatabine free base, glutaric acid, and the at least one solvent are preferably combined to form the reaction mixture at about room temperature (i.e. a range of preferably 15° C. to 25° C.). The concentration of glutaric acid present in such reaction mixture is preferably a concentration close to the point of saturation (e.g. at least 80%, preferably 90%, more preferably 95% of the maximum achievable concentration). Anatabine glutarate typically precipitates out of the mixture. The precipitation may occur on its own or be induced, e.g., by the introduction of seed crystals. The reaction mixture may be stirred before, during, or after precipitation.

The reaction mixture may be heated and then cooled to facilitate precipitation of anatabine glutarate. Heating may be carried out up to any temperature (e.g. about 50° C. to about 80° C.) in the range of from room temperature to the boiling temperature of the solvent. Thereafter, cooling is generally conducted down to less than 40° C., preferably about 30° C. to about 20° C., more preferably room temperature (i.e. a range of preferably 15° C. to 25° C.), to facilitate precipitation.

The resulting precipitate may be recovered by various techniques, such as filtration. The precipitate may be dried under ambient or reduced pressure and/or elevated temperature.

Anatabine glutarate, and particularly the polymorphic form described above, has advantageous properties such as high crystallinity, morphology, thermal and mechanical stability to polymorphic conversion and/or to dehydration, storage stability, low content of residual solvent, a lower degree of hygroscopicity, flowability, and advantageous processing and handling characteristics. Furthermore, anatabine glutarate recrystallizes as a crystalline salt even after having been exposed to moisture, when the moisture is removed by suitable measures, such as drying under vacuum.

Anatabine (for example, anatabine glutarate) can be administered to an individual to treat disorders comprising an inflammatory component, including chronic, low-level inflammation. Anatabine can be administered to an individual to reduce a symptom or a disorder comprising an NFKB-mediated inflammatory component and/or to reduce the risk of developing such a disorder. The NFKB-mediated inflammatory component may be associated with chronic inflammation which occurs, for example, in thyroiditis, cancer, arthritis, Alzheimer's disease, and multiple sclerosis. The inhalable powder comprising anatabine may have a monoamine oxidase (MAO) inhibitory effect. Additionally, or alternatively, the inhalable powder comprising anatabine may have a STAT3 phosphorylation inhibition effect.

In some embodiments, the anatabine is formulated as a salt. Any pharmaceutically acceptable salt may be used. Preferably, the anatabine salt is solid at room temperature (for example, solid at 25° C.). Suitable salts include, for example, a salt of aspartic acid ("aspartate"), gentisic acid ("gentisate"), benzoic acid ("benzoate"), fumaric acid ("fumarate"), hydrochloric acid ("hydrochlorate"), alfa-resorcylic acid ("alfa-resorcylate"), beta-resorcylic acid ("beta-resorcylate"), oxalic acid ("oxalate"), p-anisic acid ("anisate"), or glutaric acid ("glutarate"). Preferably the salt comprises glutarate, such as anatabine glutarate. Preferably, the anatabine salt is anatabine glutarate. Preferably, the anatabine glutarate is the polymorphic form described above.

Another preferred alkaloid is anabasine. Anabasine may preferably be an anabasine salt. Anabasine is a pyridine and piperidine alkaloid found in the tree tobacco plant.

Further pharmaceutically active ingredients include, for example: an antiviral compound such as acyclovir; anti-inflammatory compound such as salicylic acid, aceclofenac or ketoprofen; an antidiabetic compound such as metformin or glipizide; a antihypertensive compound such as oxprenolol; an antiemetic compound such as promethazine; an antidepressant compound such as seproxetine; an anticoagulant compound such as picotamide; a bronchodialator such as clenbuterol; or an anticancer compound such as beta-lapachone.

The beneficial crystallinity and reduced hygroscopicity may be achieved by selecting one or more parameters of the composition and the method of making the inhalable powder. For example, the active agent maybe selected such that it is solid at room temperature (for example, solid at 25° C.). The active agent may be a solid at 30° C. or below, or at 25° C. The sugar or sugar alcohol may be selected to have a suitable glass transition temperature (Tg) such that the desired crystallinity can be achieved via spray drying.

The sugar or sugar alcohol may be selected to have a glass transition temperature of 100° C. or less, 75° C. or less, or 50° C. or less, or 25° C. or less, or 0° C. or less. The sugar or sugar alcohol may be selected to have a suitable solubility in water, such as 75 g or less, 60 g or less, 50 g or less, or 30 g or less, in 100 g of water at 25° C.

The crystalline dry powder particles described herein may be formed by spray drying or freeze drying. In either method, a liquid mixture may be formed by combining the active agent (such as an alkaloid), a sugar or sugar alcohol, and optionally an amino acid. This liquid mixture is then dried or dehydrated and optionally milled to form the crystalline dry powder particles described herein. The crystalline dry powder particles may each comprise a crystalline sugar or crystalline sugar alcohol matrix and the active agent (such as an alkaloid) dispersed within the crystalline sugar or crystalline sugar alcohol matrix.

A spray drying temperature may be selected at least partly based on the selection of sugar or sugar alcohol such that the spray drying temperature is above the glass transition temperature of the sugar or sugar alcohol but also as low as possible to prevent or mitigate degradation or migration of the active agent during the spray drying process. The glass transition temperature of the sugar or sugar alcohol is below the temperature encountered by the particle during the spray drying process to ensure the necessary molecular mobility of the sugar or sugar alcohol molecule to be able to crystalize. For example, the spray drying temperature may be less than 80° C., or less than 70° C., or less than 65° C., or less than 60° C., or less than 55° C., or about 50° C. or less.

The spray drying or freeze drying method forms composite particles each containing active agent and sugar or sugar alcohol. The active agent may be dispersed within a sugar or sugar alcohol matrix. Preferably the active agent is a solid stable salt at 25° C. Preferably the active agent is a solid stable salt at 25° C. and is within a sugar or sugar alcohol crystalline matrix forming a particle or composite particle.

Preferably the sugar or sugar alcohol is a sugar alcohol. Sugar alcohols include, for example the following compounds and stereoisomers thereof, erythritol, adonitol, xylitol, arabitol, mannitol, sorbitol, myo-inositol, and the like. Preferably the sugar alcohol is selected from erythritol (Tg=−44° C.), mannitol (Tg=13° C.), myo-inositol (Tg=50° C.), stereoisomers thereof, and combinations thereof. Preferably the sugar alcohol is erythritol, mannitol, or myo-inositol.

The crystalline dry powder particles formed by spray drying or freeze drying may be milled or micronized to achieve a desired final particle size (for example, reduced from a particle size of about 50 micrometers to about 2 micrometers). The inhalable powder or crystalline dry powder particles may have a final particle size in a range from about 1 micrometre to about 5 micrometres, or form about 1 micrometre to about 3 micrometres, or from about 1.5 micrometre to about 2.5 micrometres.

The inhalable powder may further include an amino acid. Amino acid may be added to the active agent and sugar or sugar alcohol before the spray drying or freeze drying step. Amino acid may be added to the crystalline dry powder particles after the spray drying or freeze drying step. For example, the crystalline dry powder particles formed by spray drying or freeze drying may be co-milled (for example, jet-milled) with amino acid particles. The co-milling may cause the amino acid to at least partially coat the crystalline dry powder particles. The crystalline dry powder particles may be coated by an amino acid. The co-milling may further achieve a desired final particle size (for example, reduced from a particle size of about 50 micrometers to about 2 micrometers).

The combining step may include combining a sugar or sugar alcohol with an active agent, an amino acid and a liquid carrier to form a liquid mixture, and spray drying or freeze drying the liquid mixture at a temperature to form crystalline dry powder particles. The spray drying temperature is greater than a glass transition temperature of the sugar or sugar alcohol. At least selected dry powder particles each comprise an amino acid coating the crystalline dry powder particles comprising the solid active agent dispersed within a crystalline sugar matrix or crystalline sugar alcohol matrix.

The amino acid may comprise histidine, alanine, isoleucine, arginine, leucine, asparagine, lysine, aspartic acid, methionine, cysteine, phenylalanine, glutamic acid, threonine, glutamine, tryptophan, glycine, valine, pyrrolysine, proline, selenocysteine, serine, tyrosine, or a combination thereof. Preferably the amino acid comprises leucine, such as L-leucine.

The crystalline dry powder particles may comprise 5 wt-% or more or 10 wt-% or more of amino acid, and 30 wt-% or less or 25 wt-% or less of amino acid by weight of the crystalline dry powder particles. The crystalline dry powder particles may include from 5 wt-% to 30 wt-%, from 10 wt-% to 30 wt-%, from 15 wt-% to 25 wt-%, of amino acid by weight of the crystalline dry powder particles.

Preferably the crystalline dry powder particles may comprise 5 wt-% or more or 10 wt-% or more of leucine, and 30 wt-% or less or 25 wt-% or less of leucine by weight of the crystalline dry powder particles. The crystalline dry powder particles may include from 5 wt-% to 30 wt-%, from 10 wt-% to 30 wt-%, from 15 wt-% to 25 wt-%, of leucine by weight of the crystalline dry powder particles.

Providing an amino acid such as L-leucine with the crystalline dry powder particles may reduce adhesion forces of the crystalline dry powder particles and may reduce attraction between the particles and thus further reduce agglomeration of the particles.

The crystalline dry powder particles or crystalline dry powder particles may preferably form a homogenous population of particles, where each particle includes the active agent, sugar or sugar alcohol, and optional amino acid. The crystalline dry powder particles may each comprise from about 1 to about 10% active agent, from 99 to about 50% sugar or sugar alcohol, and optionally from 1 to about 40% amino acid. Preferably the crystalline dry powder particles may each comprise from about 1 to about 10% active agent, from 80 to about 70% sugar alcohol, and from 15 to about 25% amino acid.

The crystalline dry powder particles may comprise about 60% wt. or greater sugar alcohol, and 10% or greater amino acid and from about 1% to about 10% wt. solid salt of an alkaloid. At least selected particles each comprise a sugar alcohol matrix and the solid salt of an alkaloid is dispersed within the sugar alcohol matrix The crystalline dry powder particles may each comprise from about 1 to about 10% active agent, from 99 to about 60% sugar or sugar alcohol, and optionally from 10 to about 30% amino acid. Preferably the crystalline dry powder particles may each comprise from about 1 to about 10% active agent, from 85 to about 65% sugar alcohol, and from 10 to about 30% amino acid.

The crystalline dry powder particles may each comprise from about 1 to about 10% nicotine, from 99 to about 60% sugar or sugar alcohol, and optionally from 10 to about 30% amino acid. Preferably the crystalline dry powder particles may each comprise from about 1 to about 10% nicotine, from 85 to about 65% sugar alcohol, and from 10 to about 30% amino acid.

According to an aspect of the present invention, the crystalline dry powder particles comprise about 60% wt. or greater sugar alcohol, and 10% or greater amino acid and from about 1% to about 10% wt. solid alkaloid salt.

According to an aspect of the present invention, the crystalline dry powder particles may comprise a solid salt of an alkaloid, and a sugar alcohol comprising mannitol, erythritol, myo-inositol, adonitol, xylitol, or a combination thereof.

According to an aspect of the present invention, the crystalline dry powder particles may comprise a solid salt of an alkaloid, and a sugar alcohol comprising mannitol, erythritol, myo-inositol, or a combination thereof.

According to an aspect of the present invention, the crystalline dry powder particles may comprise a solid salt of an alkaloid, a sugar alcohol comprising mannitol, erythritol, myo-inositol, or a combination thereof, and leucine.

According to an aspect of the present invention, the crystalline dry powder particles may comprise nicotine aspartate, a sugar alcohol comprising mannitol, erythritol, myo-inositol, or a combination thereof, and leucine.

According to an aspect of the present invention, the crystalline dry powder particles may comprise nicotine bitartrate, a sugar alcohol comprising mannitol, erythritol, myo-inositol, or a combination thereof, and leucine.

According to an aspect of the present invention, the crystalline dry powder particles may comprise nicotine glutarate, a sugar alcohol comprising mannitol, erythritol, myo-inositol, or a combination thereof, and leucine.

According to an aspect of the present invention, the crystalline dry powder particles may comprise nicotine malate, a sugar alcohol comprising mannitol, erythritol, myo-inositol, or a combination thereof, and leucine.

According to an aspect of the present invention, the crystalline dry powder particles may comprise anatabine glutarate, a sugar alcohol comprising mannitol, erythritol, myo-inositol, or a combination thereof, and leucine.

The spray drying or freeze drying method results in crystalline dry powder particles that contain the active agent and are suitable for inhalation. Advantageously, the crystalline dry powder particles exhibit low or reduced hygroscopicity. The crystalline dry powder particles do not readily absorb water or moisture when exposed to humid or tropical conditions. The crystalline dry powder particles do not readily agglomerate when exposed to humid or tropical conditions. Further advantageously, the crystalline dry powder particles are stable and possess a long shelf life.

The present disclosure describes inhalable powders with various active agents. Preferably, the active agent comprises an alkaloid such as nicotine or anatabine or anabasine, for example. Preferably, the active agent comprises solid salt of an alkaloid.

The salt may be formed during the method (during the combining step) or may be formed before the combining step. For example, a free base active agent may be mixed with aspartic acid, gentisic acid, benzoic acid, fumaric acid, tartaric acid, lactic acid, maleic acid, muconic acid, hydrochloric acid, alfa-resorcylic acid, beta-resorcylic acid, oxalic acid, p-anisic acid, glutaric acid, or a combination thereof, preferably aspartic acid, tartaric acid or glutaric acid. The acid may be mixed with the free base active agent at any suitable ratio depending on the desired salt form and the rate of reaction. For example, a monoprotic acid such as benzoic acid may be combined with nicotine in about a 1:1 molar ratio to provide a monoprotonated nicotine salt.

The amount of active agent may be selected based on the desired or intended use of the inhalable powder. For example, the amount of active agent may be between 0.5 wt-% and 10 wt-% of the total weight of the crystalline dry powder particles. In some embodiments, the crystalline dry powder particles comprises 0.5 wt-% or more, 1 wt-% or more, 2 wt-% or more, or 3 wt-% or more of the active agent, and 12 wt-% or less, 10 wt-% or less, 9 wt-% or less, 8 wt-% or less, or 7 wt-% or less, of the active agent, or from 0.5 wt-% to 10 wt-%, from 1 wt-% to 8 wt-%, from 1.5 wt-% to 6 wt-%, or from 2 wt-% to 5 wt-of the active agent.

In some embodiments, the crystalline dry powder particles comprises 0.5 wt-% or more, 1 wt-% or more, 2 wt-% or more, or 3 wt-% or more of nicotine, and 12 wt-% or less, 10 wt-% or less, 9 wt-% or less, 8 wt-% or less, or 7 wt-% or less, of nicotine, or from 0.5 wt-% to 10 wt-%, from 1 wt-% to 8 wt-%, from 1.5 wt-% to 6 wt-%, or from 2 wt-% to 5 wt-% nicotine.

The amount of active agent may also be selected on a per-dose basis. The inhalable powder may be packaged in a single dose form or in a multiple dose form. For example, the inhalable powder may comprise 0.5 mg or more, 1 mg or more, 2 mg or more, or 5 mg or more of the active agent per dose. The inhalable powder may comprise 500 mg or less, 200 mg or less, 100 mg or less, 50 mg or less, 20 mg or less, or 10 mg or less of the active agent per dose. In some embodiments, the inhalable powder comprises from 0.01 to 10 mg of anatabine or nicotine or anabasine per dose, 0.05 to 5 mg anatabine or nicotine or anabasine per dose, or 0.1 to 1 mg of anatabine or nicotine or anabasine per dose.

The inhalable powder composition may be made by a method comprising combining sugar or a sugar alcohol with the active agent and a liquid carrier to form a liquid mixture. The liquid mixture may be spray dried or freeze dried to form crystalline dry powder particles. Preferably the liquid carrier is aqueous. Preferably the liquid carrier is water. Preferably the liquid carrier is at least about 95% water, or at least 99% water, or 100% water (based on total weight of liquid carrier).

The liquid carrier may also comprise an organic solvent, such as of an alkanol containing 1 to 8 carbon atoms, an aliphatic ester containing 3 to 8 carbon atoms, an aliphatic linear or cyclic ether containing 3 to 8 carbon atoms, an aliphatic ketone containing 3 to 8 carbon atoms, methanol, ethanol, acetone, or acetonitrile.

The liquid mixture may be spray dried at a spray drying temperature that is greater than a glass transition temperature of the sugar or sugar alcohol. The spray drying temperature may be 80° C. or less, 70° C. or less, 60° C. or less, or 50° C. or less. In some embodiments, the spray drying temperature is also selected based on the active agent. Such spray drying temperatures may be used for preparing a nicotine powder and to minimize the loss or degradation of nicotine during drying. The spray drying temperature is the outlet temperature of the spray nozzle of the spray dryer. The spray drying temperature may be the maximum temperature experienced by any give droplet during the spray drying process.

As a result of being spray dried or freeze dried from a liquid mixture of the active agent and sugar or sugar alcohol, the crystalline dry powder particles contain active agent that is dispersed throughout the particle in a sugar or sugar alcohol matrix. The matrix of crystalline sugar or crystalline sugar alcohol may help protect the active agent from environmental factors, such as high temperature and humidity. The matrix of crystalline sugar or crystalline sugar alcohol also helps minimize agglomeration and maintain good flowability and aerodynamic properties of the crystalline dry powder particles. However, once the crystalline dry powder particles reach the lungs of a user, the crystalline dry powder particles dissolve rapidly, which helps to provide fast uptake of the active agent.

The crystalline dry powder particles may have a particle size of 20 μm or less, 10 μm or less, or 5 μm or less, or 0.1 μm or greater, 0.2 μm or greater, or 0.5 μm or greater, or ranging from 0.5 μm to 10 μm, or from 0.75 μm to 5 μm, or from 1 μm to 5 μm, or from 1 μm to 3 μm, or from 1.5 μm to 2.5 μm. The desired particle size range may be achieved by spray drying, milling, sieving, or a combination thereof.

The crystalline dry powder particles may have pH (in solution) in a range recommended for human consumption. In some embodiments, the crystalline dry powder particles have a pH of 6 or less, 7 or less, or 8 or less, or between 3 and 8, or between 3 and 6, or between 6 and 8 when dissolved in water. The pH of the crystalline dry powder particles may be measured by reconstituting the powder in deionized water at a concentration of 1 mg/ml and measuring the pH of the resulting solution at standard temperature and pressure. The crystalline dry powder particles may be formulated without the use of an additional buffer. Additional buffering agents may be considered to be compounds capable of buffering (for example, salts, acids, bases, and combinations thereof) other than the acid used to form the salt with the active agent, or the amino acid included in the crystalline dry powder particles. The crystalline dry powder particles may be free of surfactants.

The crystalline dry powder particles may be further mixed with a second population of particles to form a powder system. Preferably, the second population of particles have a different particle size or larger particle size than the crystalline dry powder particles. For example, the second population of particles may have a particle size of about 20 μm or greater, or about 50 μm or greater, 200 μm or smaller, 150 μm or smaller, or in a range from 50 μm to 200 μm, or from 50 μm to 150 μm. The second population of particles may have any useful size distribution for inhalation delivery selectively into the mouth or buccal cavity of a user. The larger second population of flavourant particles may assist in delivery of the crystalline dry powder particles to the inhalation airflow to the user.

The crystalline dry powder particles and second population of particles may be combined in any useful relative amount so that the second population of particles are detected by the user when consumed with the crystalline dry powder particles. Preferably, the crystalline dry powder particles and second population of particles form at least about 90 wt-% or at least about 95 wt-% or at least about 99 wt-% or 100 wt-% of the total weight of the powder system.

The crystalline dry powder particles may be further mixed with a second population of flavourant particles to form a powder system. Preferably, the second population of flavourant particles have a different particle size or larger particle size than the crystalline dry powder particles. For example, the flavor particles may have a particle size of about 20 μm or greater, or about 50 μm or greater, 200 μm or smaller, 150 μm or smaller, or in a range from 50 μm to 200 μm, or from 50 μm to 150 μm. The second population of flavourant particles may have any useful size distribution for inhalation delivery selectively into the mouth or buccal cavity of a user. The larger second population of flavourant particles may assist in delivery of the crystalline dry powder particles to the inhalation airflow to the user.

The crystalline dry powder particles and second population of flavourant particles may be combined in any useful relative amount so that the second population of flavourant particles are detected by the user when consumed with the crystalline dry powder particles. Preferably, the crystalline dry powder particles and second population of flavourant particles form at least about 90 wt-% or at least about 95 wt-% or at least about 99 wt-% or 100 wt-% of the total weight of the powder system.

The crystalline dry powder particles or powder system may be provided in a suitable dosage form. For example, the crystalline dry powder particles or powder system may be provided in a capsule. The dosage form (for example, capsule) may be configured for use in a suitable inhaler. For example, the capsule may be utilized in an inhaler device having a capsule cavity. Air flow management through a capsule cavity of the inhaler device may cause a capsule contained therein to rotate during inhalation and consumption. The capsule may contain crystalline dry powder particles or powder system.

According to an embodiment, the crystalline dry powder particles or powder system is formulated to have reduced hygroscopicity and reduced tendency to agglomerate or clump together if water or moisture contacts the crystalline dry powder particles. Rotation of a pierced capsule may suspend and aerosolize the crystalline dry powder particles or powder system released from the pierced capsule into the inhalation air moving through the inhaler device. The optional flavor particles may be larger than the crystalline dry powder particles and may assist in transporting the crystalline dry powder particles to the user while the flavor particles preferentially deposit in the mouth or buccal cavity of the user. The crystalline dry powder particles and optional flavor particles may be delivered with the inhaler device at inhalation or air flow rates that are within conventional smoking regime inhalation or air flow rates.

The crystalline dry powder particles may comprise a therapeutically effective dose of the active agent, such as anatabine glutarate. Anatabine (for example, anatabine glutarate) can be administered to an individual to reduce a symptom or a disorder comprising an NFKB-mediated inflammatory component and/or to reduce the risk of developing such a disorder. The NFKB-mediated inflammatory component may be associated with chronic inflammation which occurs, for example, in thyroiditis, cancer, arthritis, Alzheimer's disease, and multiple sclerosis. The crystalline dry powder particles comprising anatabine may have a monoamine oxidase (MAO) inhibitory effect. Additionally, or alternatively, the crystalline dry powder particles comprising anatabine may have a STAT3 phosphorylation inhibition effect.

The sugar alcohol may be selected from erythritol, myo-inositol, adonitol, xylitol, mannitol, stereoisomers thereof, or a combination thereof. The sugar or sugar alcohol may be a non-reducing sugar or a sugar alcohol, preferably a sugar alcohol or a combination of sugar alcohols. Preferably the sugar alcohol is selected from erythritol, myo-inositol, adonitol, mannitol, and xylitol. Preferably the sugar alcohol is selected from erythritol, myo-inositol, and mannitol. Preferably the sugar alcohol is erythritol or myo-inositol.

The sugar or sugar alcohol may have a glass transition temperature of 100° C. or less, 75° C. or less, or 50° C. or less. The sugar or sugar alcohol may have a solubility of 75 g or less, 60 g or less, 50 g or less, or 30 g or less in 100 g of water at 25° C. The sugar alcohol may have a glass transition temperature of 100° C. or less, 75° C. or less, or 50° C. or less. The sugar alcohol may have a solubility of 75 g or less, 60 g or less, 50 g or less, or 30 g or less in 100 g of water at 25° C.

The crystalline dry powder particles may exhibit a hygroscopicity of about 5% or less. The crystalline dry powder particles may exhibit a hygroscopicity of about 4% or less. The crystalline dry powder particles may exhibit a hygroscopicity of about 3% or less. The crystalline dry powder particles may exhibit a hygroscopicity of about 2.5% or less. The crystalline dry powder particles may exhibit a hygroscopicity of about 2% or less. The crystalline dry powder particles may exhibit a hygroscopicity of about 1.5% or less. The crystalline dry powder particles may exhibit a hygroscopicity of about 1% or less. The crystalline dry powder particles may exhibit a hygroscopicity in a range from 0% to about 5%, or 0% to about 4%, or 0% to about 3%, or 0% to about 2%.

Hygroscopicity may be measured by measuring the water uptake or absorption (wt % increase) of the sample at tropical conditions (75% relative humidity and 30 degrees Celsius atmosphere) over a 20-minute time duration. Prior to exposure to tropical condition, the sample is equilibrated at 0% relative humidity, and 25 degrees Celsius atmosphere for 24 hours to reduce or remove non-bonded water from the sample. The hygroscopicity value is measured utilizing a "Vapor Sorption Analyzer SPSx-1u High Load" manufactured by ProUmid GmbH & Co. KG, as described in the Examples below.

The crystalline dry powder particles may be made by mixing the active agent with an acid or base, the sugar or sugar alcohol, and the liquid carrier into a flowable liquid mixture, and spray drying the flowable mixture. The crystalline dry powder particles may be made by mixing the active agent with an acid or base, the sugar alcohol, and the liquid carrier into a flowable liquid mixture, and spray drying the flowable mixture. The use of an acid or base may lead to the formation of a salt of the active agent which is solid at room temperature. This may be advantageous as it allows the incorporation of active agents which are not solid at room temperature or may provide a solid with preferable physical properties. The method may further comprise adding an amino acid to the crystalline dry powder particles or flowable liquid mixture. The method may further comprise combining an amino acid with the sugar, active agent, and acid to form the mixture. The method may further comprise adding an amino acid to both the liquid mixture and to the particles.

The crystalline dry powder particles may be made by mixing the active agent with an acid, the sugar or sugar alcohol, and the liquid carrier into a flowable liquid mixture, and spray drying the flowable mixture. The crystalline dry powder particles may be made by mixing the active agent with an acid, the sugar alcohol, and the liquid carrier into a flowable liquid mixture, and spray drying the flowable mixture. The use of an acid may lead to the formation of a salt of the active agent which is solid at room temperature. This may be advantageous as it allows the incorporation of active agents which are not solid at room temperature or may provide a solid with preferable physical properties. This has been found to be particularly useful when the active agent is an alkaloid, specifically when the active agent is nicotine or anatabine or anabasine. The acid may be selected to reduce any losses of the active during the spray drying process. Malate salts have been found to be particularly effective at reducing such losses of alkaloids, particularly nicotine, during spray drying. The method may further comprise adding an amino acid to the crystalline dry powder particles. The method may further comprise combining an amino acid with the sugar, active agent, and acid to form the mixture. The method may further comprise adding an amino acid to both the liquid mixture and to the crystalline dry powder particles.

Preferably at least selected crystalline dry powder particles each comprise a solid alkaloid salt dispersed within a crystalline mannitol matrix, crystalline erythritol matrix, or crystalline myo-inositol matrix.

Preferably at least selected crystalline dry powder particles each comprise a solid nicotine salt dispersed within a crystalline mannitol matrix, crystalline erythritol matrix, or crystalline myo-inositol matrix.

Preferably at least selected crystalline dry powder particles each comprise a solid anatabine salt dispersed within a crystalline mannitol matrix, crystalline erythritol matrix, or crystalline myo-inositol matrix.

The crystalline dry powder particles may comprise nicotine aspartate; mannitol, myo-inositol, or erythritol; and leucine. The crystalline dry powder particles may comprise from 1 wt-% to 10 wt-% nicotine aspartate, from 70 wt-% to 99 wt-% mannitol, myo-inositol, or erythritol, and from 0 wt-% to 29 wt-% leucine. The crystalline dry powder particles may comprise from 1 wt-% to 10 wt-% nicotine aspartate, from 70 wt-% to 80 wt-% mannitol, myo-inositol, or erythritol, and from 15 wt-% to 25 wt-% leucine.

The crystalline dry powder particles may comprise nicotine bitartrate; mannitol, myo-inositol, or erythritol; and leucine. The crystalline dry powder particles may comprise from 1 wt-% to 10 wt-% nicotine bitartrate, from 70 wt-% to 80 wt-% mannitol, myo-inositol, or erythritol, and from 15 wt-% to 25 wt-% leucine.

The crystalline dry powder particles may comprise nicotine glutarate; mannitol, myo-inositol, or erythritol; and leucine. The crystalline dry powder particles may comprise from 1 wt-% to 10 wt-% nicotine glutarate, from 70 wt-% to 80 wt-% mannitol, myo-inositol, or erythritol, and from 15 wt-% to 25 wt-% leucine.

The crystalline dry powder particles may comprise nicotine malate; mannitol, myo-inositol, or erythritol; and leucine. The crystalline dry powder particles may comprise from 1 wt-% to 10 wt-% nicotine glutarate, from 70 wt-% to 80 wt-% mannitol, myo-inositol, or erythritol, and from 15 wt-% to 25 wt-% leucine.

The crystalline dry powder particles may comprise anatabine glutarate; mannitol, myo-inositol, or erythritol; and leucine. The crystalline dry powder particles may comprise from 1 wt-% to 10 wt-% anatabine glutarate, from 70 wt-% to 80 wt-% mannitol, myo-inositol, or erythritol, and from 15 wt-% to 25 wt-% leucine.

The crystalline dry powder particles may comprise nicotine aspartate; erythritol; and leucine. The crystalline dry powder particles may comprise from 1 wt-% to 10 wt-% nicotine aspartate, from 70 wt-% to 99 wt-% erythritol, and from 0 wt-% to 29 wt-% leucine. The crystalline dry powder particles may comprise from 1 wt-% to 10 wt-% nicotine aspartate, from 70 wt-% to 80 wt-% erythritol, and from 15 wt-% to 25 wt-% leucine.

The crystalline dry powder particles may comprise nicotine bitartrate; erythritol; and leucine. The crystalline dry powder particles may comprise from 1 wt-% to 10 wt-% nicotine bitartrate, from 70 wt-% to 80 wt-% erythritol, and from 15 wt-% to 25 wt-% leucine.

The crystalline dry powder particles may comprise nicotine glutarate; erythritol; and leucine. The crystalline dry powder particles may comprise from 1 wt-% to 10 wt-% nicotine glutarate, from 70 wt-% to 80 wt-% erythritol, and from 15 wt-% to 25 wt-% leucine.

The crystalline dry powder particles may comprise nicotine malate; erythritol; and leucine. The crystalline dry powder particles may comprise from 1 wt-% to 10 wt-% nicotine glutarate, from 70 wt-% to 80 wt-% erythritol, and from 15 wt-% to 25 wt-% leucine.

The crystalline dry powder particles may comprise anatabine glutarate; erythritol; and leucine. The crystalline dry powder particles may comprise from 1 wt-% to 10 wt-% anatabine glutarate, from 70 wt-% to 80 wt-% erythritol, and from 15 wt-% to 25 wt-% leucine.

In some embodiments, the crystalline dry powder particles may be free of mannitol when the active agent is aspartate.

The crystalline dry powder particles of the present disclosure results in a matrix of crystalline sugar or crystalline sugar alcohol that helps protect the active agent from environmental factors, such as high temperature and humidity. The matrix of crystalline sugar or crystalline sugar alcohol also helps minimize agglomeration and maintain good flowability and aerodynamic properties of the inhalable powder. However, once the inhalable powder reaches the lungs of a user, the particles dissolve rapidly, which helps to provide fast uptake of the active agent.

The lower hygroscopicity of the crystalline dry powder particles may help minimize losses of the composition due to agglomeration, stickiness, or liquification. This may provide improved control of the particle size of the crystalline dry powder particles, the size of the dose and the chemical composition of the crystalline dry powder particles delivered to the consumer. In addition to having lower hygroscopicity and thus increased shelf life, the crystalline dry powder particles may advantageously have improved aerodynamic properties. For example, a consumer may be able to consume more than half the crystalline dry powder particles contained in a cartridge or capsule. Because the crystalline dry powder particles does not readily absorb water, a consumer may be able to get more usage sessions or puffs from a single cartridge or capsule. The crystalline dry powder particles may also be provided in larger dosage forms, such as cartridges or capsules, due to the fact that the quality of the crystalline dry powder particles is not compromised soon after opening of the package.

The term "particle size" is used here to refer to the mass median aerodynamic diameter (MMAD) of the particle or set of particles, unless otherwise stated. Such values are based on the distribution of the aerodynamic particle diameters defined as the diameter of a sphere with a density of 1 $gm/cm^3$ that has the same aerodynamic behavior as the particle which is being characterized.

In particular, for a powder system reference is commonly made to the mass median aerodynamic diameter (MMAD), one of the metrics most widely adopted as a single number descriptor of aerodynamic particle-size distribution. The MMAD is a statistically derived figure for a particle sample: by way of example, an MMAD of 5 micrometres means that 50 percent of the total sample mass will be present in particles having aerodynamic diameters of less than 5 micrometres, and that the remaining 50 percent of the total sample mass will be present in particles having an aerodynamic diameter greater than 5 micrometres. In the context of the present invention, when describing a powder system, the term "particle size" preferably refers to the MMAD of the powder system.

The MMAD of a powder system is preferably measured with a cascade impactor. Cascade impactors are instruments which have been extensively used for sampling and separating airborne particles for determining the aerodynamic size classification of aerosol particles. In practice, cascade impactors separate an incoming sample into discrete fractions on the basis of particle inertia, which is a function of particle size, density and velocity. A cascade impactor typically comprises a series of stages, each of which comprises a plate with a specific nozzle arrangement and a collection surface. As nozzle size and total nozzle area both decrease with increasing stage number, the velocity of the sample-laden air increases as it proceeds through the instrument. At each stage, particles with sufficient inertia break free from the prevailing air stream to impact on the collection surface. Therefore, at any given flow rate, each stage is associated with a cut-off diameter, a figure that defines the size of particles collected. With increasing stage number, velocity increases and so stage cut-off diameter decreases. Thus, the cut-off diameter associated with a given stage is a function of the air-flow rate used for testing. To reflect in-use performance, nebulisers are routinely tested at 15 L/min and dry powder inhalers may be tested at flow rates up to 100 L/min.

Preferably, in the context of the present invention, the MMAD of a powder system is measured with a Next Generation Impactor (NGI) 170 (available from Copley Scientific AG). The NGI is a high performance, precision, particle classifying cascade impactor having seven stages plus a Micro-Orifice Collector (MOC). Characteristics and operation principle of a NGI are described, for example, in Marple et al., Journal of Aerosol Medicine—Volume 16, Number 3 (2003). More preferably, measurements are carried out at 20±3 degrees Celsius and relative humidity of 35±5 percent.

A dry powder formulation typically contains less than or equal to about 15 percent by weight moisture, preferably less than or equal to about 10 percent moisture, even more preferably less than or equal to about 6 percent by weight moisture. Most preferably a dry powder formulation contains less than or equal to about 5 percent by weight moisture or even less than or equal to about 3 percent by weight moisture or even less than or equal to about 1 percent by weight moisture.

All values reported as a percentage are presumed to be weight percent based on the total weight.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

The term "substantially" as used here has the same meaning as "significantly," and can be understood to modify the relevant term by at least about 90%, at least about 95%, or at least about 98%. The term "not substantially" as used here has the same meaning as "not significantly," and can be understood to have the inverse meaning of "substantially," i.e., modifying the relevant term by not more than 10%, not more than 5%, or not more than 2%.

The invention is defined in the claims. However, below there is provided a non-exhaustive listing of non-limiting examples. Any one or more of the features of these examples may be combined with any one or more features of another example, embodiment, or aspect described herein.

Example Ex1. An inhalable powder includes crystalline dry powder particles. The crystalline dry powder particles include a solid salt of an alkaloid and a sugar alcohol.

Example Ex2. The inhalable powder of Ex1, wherein the sugar alcohol is mannitol, erythritol, myo-inositol, adonitol, xylitol, or a combination thereof.

Example Ex3. The inhalable powder of any preceding Example, wherein the sugar alcohol is mannitol, erythritol, myo-inositol, or a combination thereof.

Example Ex4. The inhalable powder of any preceding Example, wherein the sugar alcohol is mannitol.

Example Ex5. The inhalable powder of any preceding Example, wherein the sugar alcohol is erythritol.

Example Ex6. The inhalable powder of any preceding Example, wherein the sugar alcohol is myo-inositol.

Example Ex7. The inhalable powder of any preceding Example, wherein the solid salt of an alkaloid is a nicotine salt.

Example Ex8. The inhalable powder of any preceding Example, wherein the solid salt of an alkaloid comprises nicotine bitartrate, nicotine aspartate, nicotine malate, or nicotine glutarate.

Example Ex9. The inhalable powder of any preceding Example, wherein the solid salt of an alkaloid is nicotine bitartrate.

Example Ex10. The inhalable powder of any preceding Example, wherein the solid salt of an alkaloid is nicotine aspartate.

Example Ex11. The inhalable powder of any preceding Example, wherein the solid salt of an alkaloid is nicotine glutarate.

Example Ex12. The inhalable powder of any preceding Example, wherein the solid salt of an alkaloid is nicotine malate.

Example Ex13. The inhalable powder of any preceding Example, wherein the solid salt of an alkaloid comprises an anatabine salt.

Example Ex14. The inhalable powder of any preceding Example, wherein the solid salt of an alkaloid is anatabine glutarate.

Example Ex15. The inhalable powder of any preceding Example, wherein the solid salt of an alkaloid is anabasine.

Example Ex16. The inhalable powder of any preceding Example, wherein the crystalline dry powder particles comprises a solid salt of an alkaloid, a sugar alcohol, and an amino acid.

Example Ex17. The inhalable powder of any preceding Example, wherein the crystalline dry powder particles comprises a solid salt of an alkaloid, a sugar alcohol, and leucine.

Example Ex18. The inhalable powder of any preceding Example, wherein the crystalline dry powder particles comprises nicotine bitartrate, nicotine aspartate, nicotine malate, or nicotine glutarate, a sugar alcohol, and leucine.

Example Ex19. The inhalable powder of any preceding Example, wherein the crystalline dry powder particles comprises nicotine bitartrate, nicotine aspartate, nicotine malate, or nicotine glutarate, mannitol, and leucine.

Example Ex20. The inhalable powder of any preceding Example, wherein the crystalline dry powder particles comprises nicotine bitartrate, nicotine aspartate, nicotine malate, or nicotine glutarate, erythritol, and leucine.

Example Ex21. The inhalable powder of any preceding Example, wherein the crystalline dry powder particles comprises nicotine bitartrate, nicotine aspartate, nicotine malate, or nicotine glutarate, myo-inositol, and leucine.

Example Ex22. The inhalable powder of any preceding Example, wherein the crystalline dry powder particles comprises nicotine bitartrate, mannitol, and leucine, and at least selected crystalline dry powder particles each comprise a mannitol matrix and the nicotine bitartrate is dispersed within the mannitol matrix.

Example Ex23. The inhalable powder of any preceding Example, wherein the crystalline dry powder particles comprises nicotine bitartrate, erythritol, and leucine, and at least selected crystalline dry powder particles each comprise a erythritol matrix and the nicotine bitartrate is dispersed within the erythritol matrix.

Example Ex24. The inhalable powder of any preceding Example, wherein the crystalline dry powder particles comprises nicotine bitartrate, myo-inositol, and leucine, and at least selected crystalline dry powder particles each comprise a myo-inositol matrix and the nicotine bitartrate is dispersed within the myo-inositol matrix.

Example Ex25. The inhalable powder of any preceding Example, wherein the crystalline dry powder particles comprises nicotine aspartate, mannitol, and leucine, and at least selected crystalline dry powder particles each comprise a mannitol matrix and the nicotine aspartate is dispersed within the mannitol matrix.

Example Ex26. The inhalable powder of any preceding Example, wherein the crystalline dry powder particles comprises nicotine aspartate, erythritol, and leucine, and at least selected crystalline dry powder particles each comprise a erythritol matrix and the nicotine aspartate is dispersed within the erythritol matrix.

Example Ex27. The inhalable powder of any preceding Example, wherein the crystalline dry powder particles comprises nicotine aspartate, myo-inositol, and leucine, and at least selected crystalline dry powder particles each comprise a myo-inositol matrix and the nicotine aspartate is dispersed within the myo-inositol matrix.

Example Ex28. The inhalable powder of any preceding Example, wherein the crystalline dry powder particles comprises nicotine glutarate, mannitol, and leucine, and at least selected crystalline dry powder particles each comprise a mannitol matrix and the nicotine glutarate is dispersed within the mannitol matrix.

Example Ex29. The inhalable powder of any preceding Example, wherein the crystalline dry powder particles comprises nicotine glutarate, erythritol, and leucine, and at least selected crystalline dry powder particles each comprise a erythritol matrix and the nicotine glutarate is dispersed within the erythritol matrix.

Example Ex30. The inhalable powder of any preceding Example, wherein the crystalline dry powder particles comprises nicotine glutarate, myo-inositol, and leucine, and at least selected crystalline dry powder particles each comprise a myo-inositol matrix and the nicotine glutarate is dispersed within the myo-inositol matrix.

Example Ex31. The inhalable powder of any preceding Example, wherein the crystalline dry powder particles comprises nicotine malate, mannitol, and leucine, and at least selected crystalline dry powder particles each comprise a mannitol matrix and the nicotine malate is dispersed within the mannitol matrix.

Example Ex32. The inhalable powder of any preceding Example, wherein the crystalline dry powder particles comprises nicotine malate, erythritol, and leucine, and at least selected crystalline dry powder particles each comprise a erythritol matrix and the nicotine malate is dispersed within the erythritol matrix.

Example Ex33. The inhalable powder of any preceding Example, wherein the crystalline dry powder particles comprises nicotine malate, myo-inositol, and leucine, and at least selected crystalline dry powder particles each comprise a myo-inositol matrix and the nicotine malate is dispersed within the myo-inositol matrix.

Example Ex34. The inhalable powder of any preceding Example, wherein the crystalline dry powder particles comprise about 60% wt. or greater sugar alcohol, and 10% or greater amino acid and from about 1% to about 10% wt. solid alkaloid salt.

Example Ex35. The inhalable powder of any preceding Example, wherein the crystalline dry powder particles comprise about 60% wt. or greater sugar alcohol, and 10% or greater amino acid and from about 1% to about 10% wt. solid alkaloid salt, and at least selected crystalline dry powder particles each comprise a sugar alcohol matrix and the solid salt of an alkaloid is dispersed within the sugar alcohol matrix.

Example Ex36. The inhalable powder of any preceding Example, wherein the crystalline dry powder particles comprise 70% to 80% erythritol, 15% to 25% leucine, and 1% to 10% nicotine bitartrate, and at least selected crystalline dry powder particles each comprise a erythritol matrix and the nicotine bitartrate is dispersed within the erythritol matrix.

Example Ex37. The inhalable powder of any preceding Example, wherein the crystalline dry powder particles comprise 70% to 80% erythritol, 15% to 25% leucine, and 1% to 10% nicotine aspartate, and at least selected crystalline dry powder particles each comprise a erythritol matrix and the nicotine aspartate is dispersed within the erythritol matrix.

Example Ex38. The inhalable powder of any preceding Example, wherein the crystalline dry powder particles comprise 70% to 80% erythritol, 15% to 25% leucine, and 1% to 10% nicotine glutarate, and at least selected crystalline dry powder particles each comprise a erythritol matrix and the nicotine glutarate is dispersed within the erythritol matrix.

Example Ex39. The inhalable powder of any preceding Example, wherein the crystalline dry powder particles comprise 70% to 80% erythritol, 15% to 25% leucine, and 1% to 10% nicotine malate, and at least selected crystalline dry powder particles each comprise a erythritol matrix and the nicotine malate is dispersed within the erythritol matrix.

Example Ex40. The inhalable powder of any preceding Example, wherein the crystalline dry powder particles comprise 70% to 80% myo-inositol, 15% to 25% leucine, and 1% to 10% nicotine bitartrate, and at least selected crystalline dry powder particles each comprise a myo-inositol matrix and the nicotine bitartrate is dispersed within the myo-inositol matrix.

Example Ex41. The inhalable powder of any preceding Example, wherein the crystalline dry powder particles comprise 70% to 80% myo-inositol, 15% to 25% leucine, and 1% to 10% nicotine aspartate, and at least selected crystalline dry powder particles each comprise a myo-inositol matrix and the nicotine aspartate is dispersed within the myo-inositol matrix.

Example Ex42. The inhalable powder of any preceding Example, wherein the crystalline dry powder particles comprise 70% to 80% myo-inositol, 15% to 25% leucine, and 1% to 10% nicotine glutarate, and at least selected crystalline dry powder particles each comprise a myo-inositol matrix and the nicotine glutarate is dispersed within the myo-inositol matrix.

Example Ex43. The inhalable powder of any preceding Example, wherein the crystalline dry powder particles comprise 70% to 80% myo-inositol, 15% to 25% leucine, and 1% to 10% nicotine malate, and at least selected crystalline dry powder particles each comprise a myo-inositol matrix and the nicotine malate is dispersed within the myo-inositol matrix.

Example Ex44. The inhalable powder of any preceding Example, wherein the crystalline dry powder particles comprise 70% to 80% mannitol, 15% to 25% leucine, and 1% to 10% nicotine bitartrate, and at least selected crystalline dry powder particles each comprise a mannitol matrix and the nicotine bitartrate is dispersed within the mannitol matrix.

Example Ex45. The inhalable powder of any preceding Example, wherein the crystalline dry powder particles comprise 70% to 80% mannitol, 15% to 25% leucine, and 1% to 10% nicotine aspartate, and at least selected crystalline dry powder particles each comprise a mannitol matrix and the nicotine aspartate is dispersed within the mannitol matrix.

Example Ex46. The inhalable powder of any preceding Example, wherein the crystalline dry powder particles comprise 70% to 80% mannitol, 15% to 25% leucine, and 1% to 10% nicotine glutarate, and at least selected crystalline dry powder particles each comprise a mannitol matrix and the nicotine glutarate is dispersed within the mannitol matrix.

Example Ex46. The inhalable powder of any preceding Example, wherein the crystalline dry powder particles comprise 70% to 80% mannitol, 15% to 25% leucine, and 1% to 10% nicotine malate, and at least selected crystalline dry powder particles each comprise a mannitol matrix and the nicotine malate is dispersed within the mannitol matrix.

Example Ex.47 The inhalable powder of any preceding Example, wherein the crystalline dry powder particles have a hygroscopicity of 5% or less, or 4% or less, or 3% or less, or 2% or less.

Example Ex.48 An inhalable powder system comprising a first population of crystalline dry powder particles of the powder of any one or more preceding Examples and a second population of particles having a particle size greater than that of the first population of particles.

Example Ex.49 The inhalable powder system of Ex48, wherein the first population of crystalline dry powder particles has a particle size of from about 1 micrometre to about 5 micrometres and the second population of particles has a particle size of from 20 micrometres to 200 micrometres.

The Examples will now be further described with reference to the figures in which.

Figure 1:
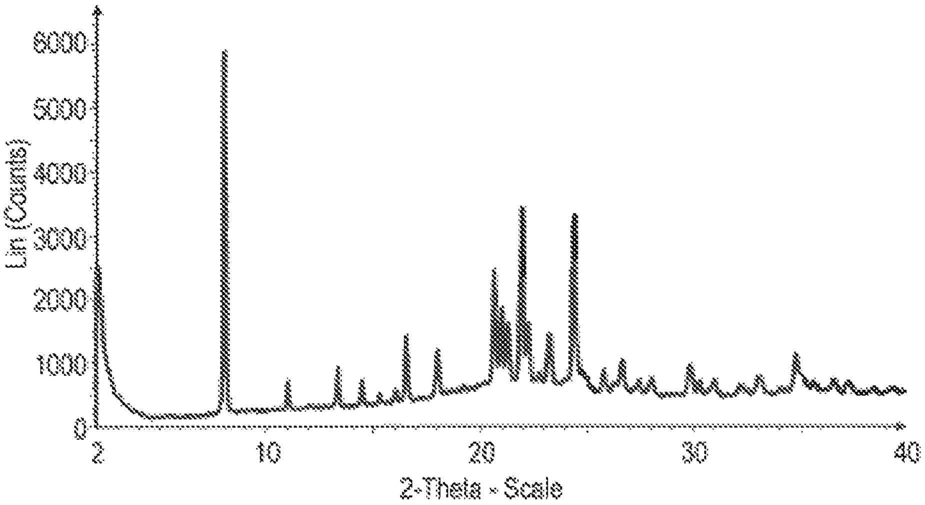
FIG. 1 is an X-ray powder diffraction pattern (CuKα) of a preferred polymorph of anatabine glutarate.
Figure 2:
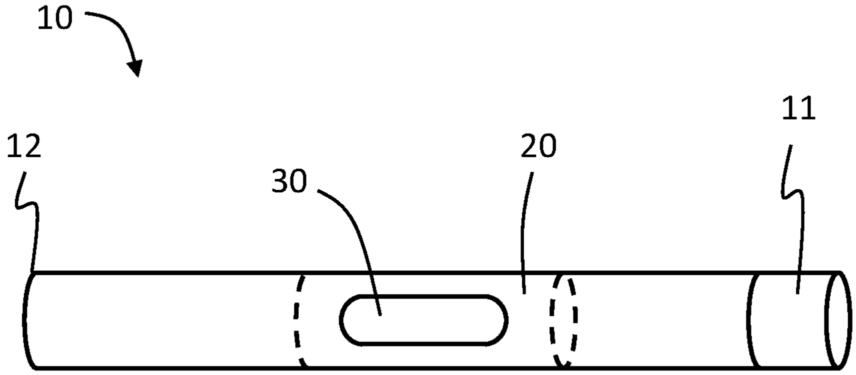
FIG. 2 is a schematic diagram of an illustrative inhaler article.

The illustrative inhaler article 10 of FIG. 2 includes an elongated cylindrical body extending from a mouthpiece end 11 to a distal end 12. A capsule cavity 20 is defined within the elongated cylindrical body. A capsule 30 is contained within the capsule cavity 20. Crystalline dry powder particles described herein may be contained within the capsule 30. The capsule 30 may be pierced to form an aperture through the body of the capsule 30 and inhalation air may flow through the inhaler article 10 to release crystalline dry powder particles from the pierced capsule 30 and into the inhalation airflow and out of the mouthpiece end 11.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

EXAMPLES

A first liquid mixture was formed by combining 2.5% free base nicotine, 20% leucine, 73.4% mannitol, 4.1% aspartic acid in water. The first liquid mixture was fed to a spray dryer (Buchi B-290) operating with a first condition set (1.0 bar, 50° C. and 2.5 g/min feed rate) and a second condition set (3.0 bar, 50° C. and 2.5 g/min feed rate) to form crystalline dry powder particles.

Crystalline dry powder particles produced from the first condition set produced a fine, free-flowing white powder. This powder had a particle size distribution of: $X_{10}$=1.78 micrometer, $X_{50}$=7.13 micrometers, $X_{90}$=14.56 micrometers, and VMD=7.82 micrometers. These crystalline dry powder particles are then co-micronized (fluid energy mill) with leucine at a ratio 85:15 (crystalline dry powder particles:leucine). This co-micronized powder had a particle size distribution of: $X_{10}$=0.64 micrometer, $X_{50}$=1.29 micrometers, $X_{90}$=2.81 micrometers, and VMD=1.54 micrometers.

Crystalline dry powder particles produced from the second condition set produced a fine, free-flowing white powder. This powder had a particle size distribution of: $X_{10}$=1.10 micrometer, $X_{50}$=2.88 micrometers, $X_{90}$=6.13 micrometers, and VMD=3.37 micrometers.

Additional crystalline dry powder particles are formed (utilizing the formulations listed in Table 1 below) utilizing the spray drying second condition set described above. All of the samples and comparative examples had a particle size distribution of about: $X_{50}$=2-4 micrometers, and $X_{90}$=5-6 micrometers.

TABLE 1

| Sample | Nicotine % | Aspartic Acid % | Leucine % | Sugar or Sugar Alcohol % |
|---|---|---|---|---|
| A | 2.5 | 4.1 | 20 | 73.4 - Mannitol Tg = 13° C. |
| B | 2.5 | 4.1 | 20 | 73.4 - Myo-Inositol Tg = <50° C. |
| C | 2.5 | 4.1 | 20 | 73.4 - Erythritol Tg = −44° C. |
| D | 2.5 | 4.1 | 20 | 73.4 - Adonitol Tg = −21° C. |
| E | 2.5 | 4.1 | 20 | 73.4 - Xylitol Tg = −29° C. |

A comparative sample "Comp Ex" is produced utilizing an amorphous sugar trehalose (Tg=106° C. and solubility 69 g/100 ml water at 25° C.) utilizing a comparative liquid mixture formed by combining 2.5% free base nicotine, 10% leucine, 86.25% trehalose, 1.25% lactic acid in water. The comparative liquid mixture was fed to a spray dryer (Buchi B-290) operating with a first condition set (5.5 bar, 70° C. and 3 g/min feed rate) to form amorphous dry powder particles.

Powder x-ray diffraction measurements are performed using a PANalytical X'Pert Pro diffractometer equipped with a CuKα radiation source (λ=1.5432 nm, 40 kV, 40 mA) in Bragg-Brentano geometry using standard sample holders. Six, 30 minute scans were performed on each sample. FIGS. 3-8 are the resulting patterns or graphs of these powder x-ray diffraction measurements.

Figure 3:
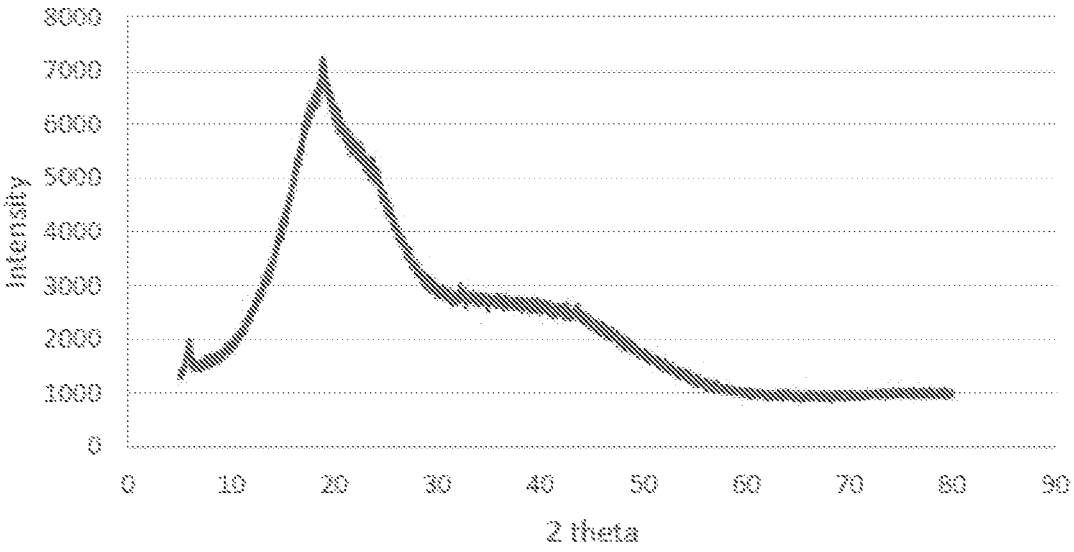
FIG. 3 is a powder X-ray diffraction pattern for Comp Ex amorphous trehalose powder formulation described below.

FIG. 3 is a powder X-ray diffraction pattern for Comp Ex trehalose powder formulation. This pattern indicates Comp Ex is largely amorphous.

Figure 4:
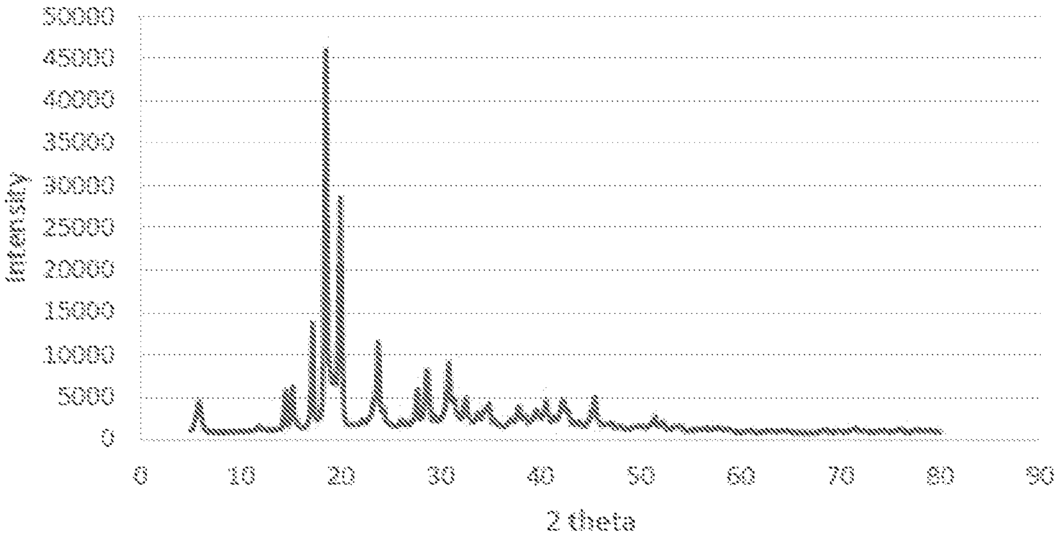
FIG. 4 is a powder X-ray diffraction pattern for Sample B crystalline myo-inositol powder formulation described below.

FIG. 4 is a powder X-ray diffraction pattern for Sample B crystalline myo-inositol powder formulation. This pattern indicates Sample B is crystalline.

Figure 5:
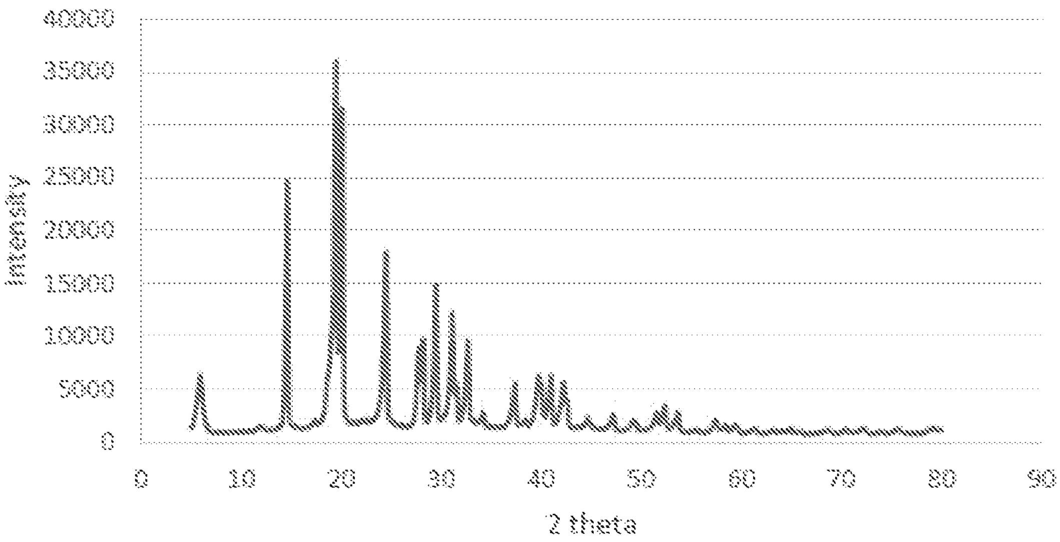
FIG. 5 is a powder X-ray diffraction pattern for Sample C crystalline erythritol powder formulation described below.

FIG. 5 is a powder X-ray diffraction pattern for Sample C crystalline erythritol powder formulation. This pattern indicates Sample C is crystalline.

Figure 6:
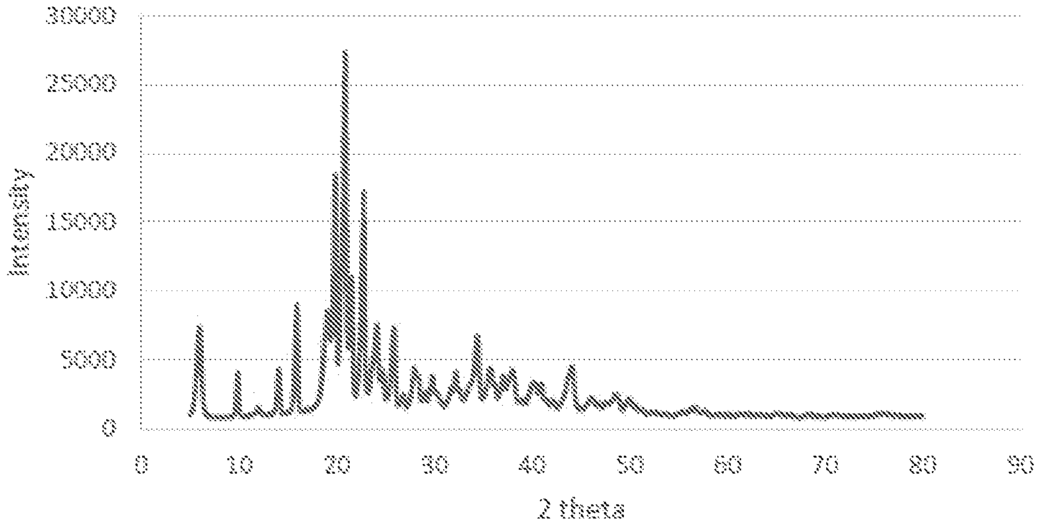
FIG. 6 is a powder X-ray diffraction pattern for Sample D crystalline adonitol powder formulation described below.

FIG. 6 is a powder X-ray diffraction pattern for Sample D crystalline adonitol powder formulation. This pattern indicates Sample D is crystalline.

Figure 7:
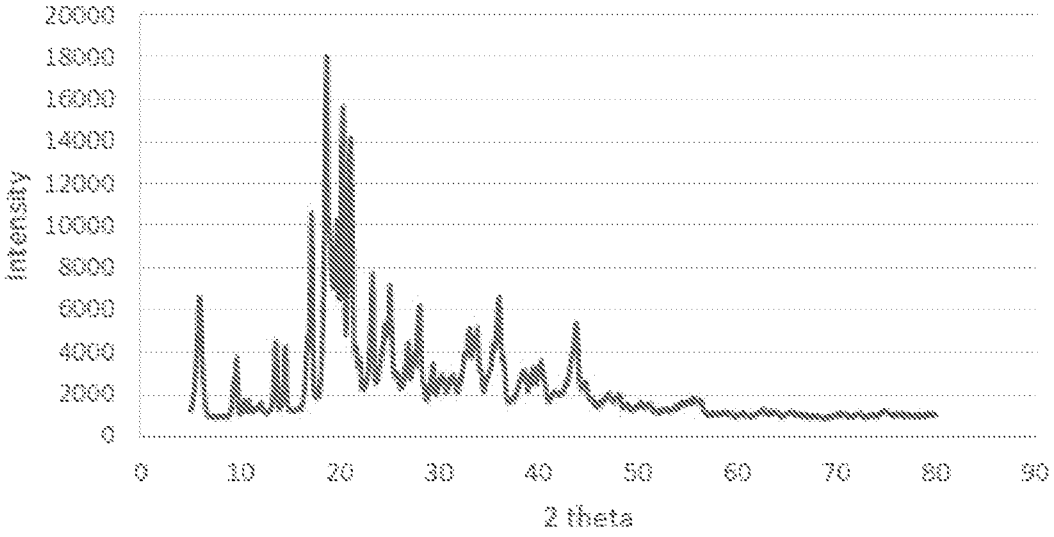
FIG. 7 is a powder X-ray diffraction pattern for Sample A crystalline mannitol powder formulation described below.

FIG. 7 is a powder X-ray diffraction pattern for Sample A crystalline mannitol powder formulation. This pattern indicates Sample A is crystalline.

Figure 8:
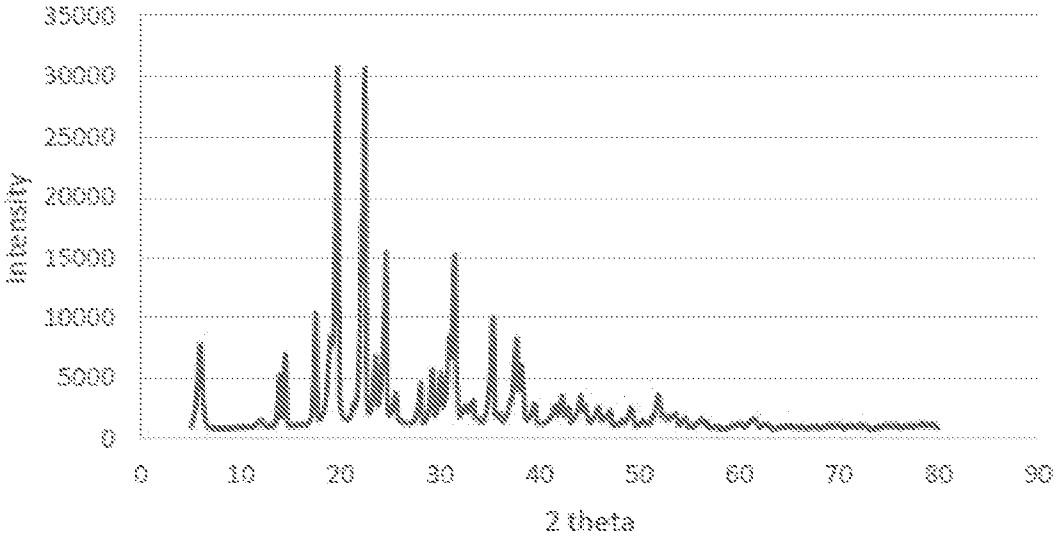
FIG. 8 is a powder X-ray diffraction pattern for Sample E crystalline xylitol powder formulation described below.

FIG. 8 is a powder X-ray diffraction pattern for Sample E crystalline xylitol powder formulation. This pattern indicates Sample E is crystalline.

Figure 9:
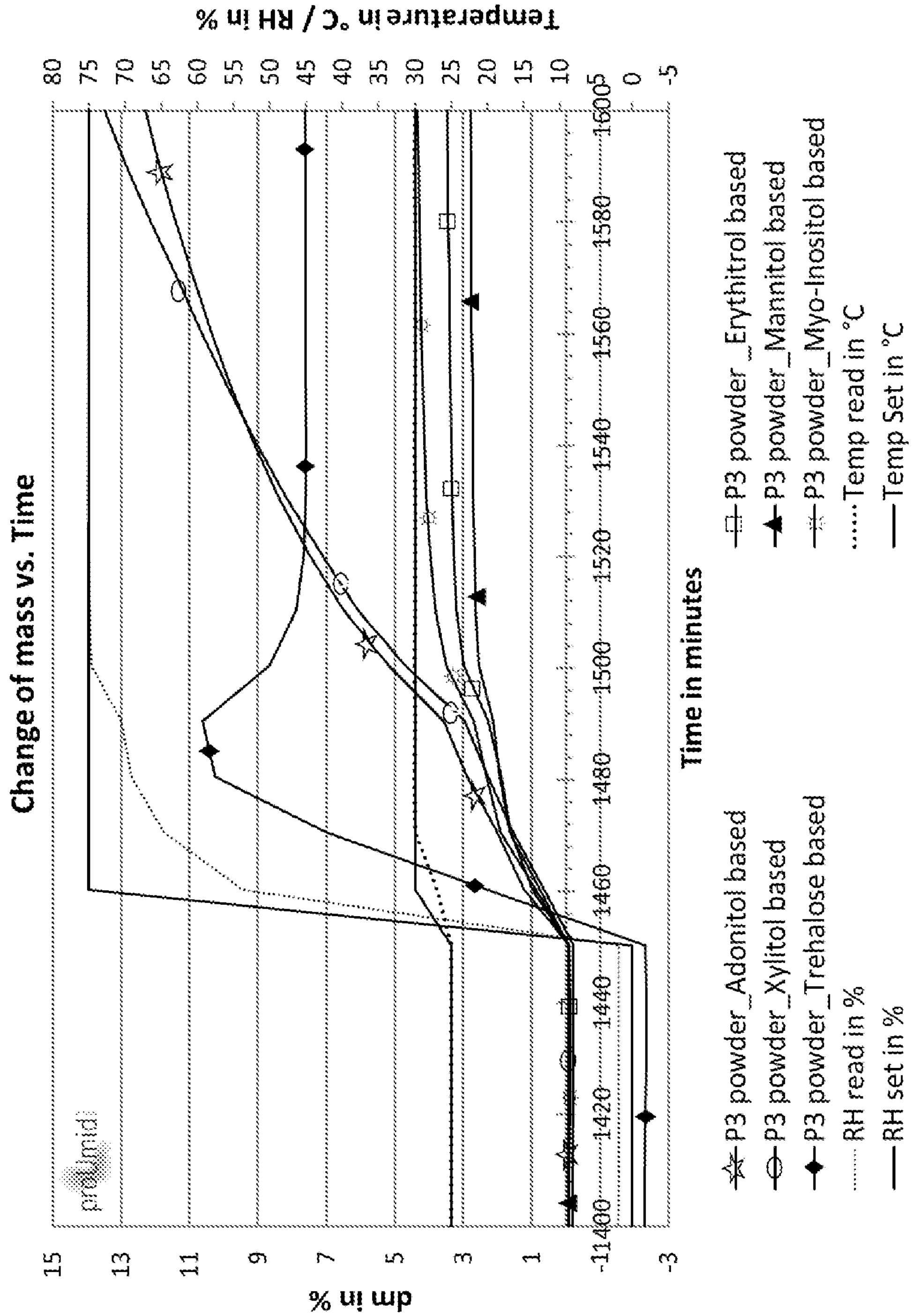
FIG. 9 is a graph of the hygroscopicity test data described in the examples below.

As illustrated in FIG. 9, each of the 100 milligram samples (Samples A-E and Comp Ex) were placed into the measuring chamber of the ProUmid Vapor Sorption instrument and equilibrated at 0% relative humidity and 25 degrees Celsius for 24 hours 1450 minutes). Then the instrument temperature was raised to 30 degrees Celsius and 75% relative humidity. Measurements were taken about every 6 minutes.

The trehalose based sample (Comp Ex) exhibited the greatest rate of mass (moisture uptake) increase of over 7% at 20 minutes and over 10% at 30 minutes.

The mannitol based (Sample A), myo-inositol based (Sample B), erythritol based (Sample C), adonitol based (Sample D), and the xylitol based (Sample E) all exhibited an increase of 2% or less at 20 minutes and 3% or less at 30 minutes. Table 2 below illustrate the hygroscopicity from 1450 min to 1500 min (50 minute duration).

TABLE 2

| | Mass % Increase verses Time | | | | | |
|---|---|---|---|---|---|---|
| Time (min) | Comp Ex Trehalose | Sample A Mannitol | Sample B Myo-inositol | Sample C Erythritol | Sample D Adonitol | Sample E Xylitol |
| 0 | 0 | 0 | 0 | 0 | 0 | 0 |
| 10 | 2.3 | 0.8 | 0.9 | 1.0 | 1.2 | 0.6 |
| 20 | 7 | 1.6 | 1.9 | 1.6 | 2.0 | 1.5 |
| 30 | 10 | 1.9 | 2.3 | 1.9 | 2.9 | 2.3 |
| 40 | 10 | 2.1 | 2.7 | 2.2 | 3.6 | 3.0 |
| 50 | 9.5 | 2.5 | 3.5 | 3..0 | 5.4 | 4.8 |

Next all the samples are tested using an aerosol generation test under tropical conditions. About 50 grams of each sample powder was loaded into a capsule and the capsule was placed into an inhaler device and pierced. Inhalation air (75% relative humidity and 30 degrees Celsius) was passed through the inhaler at a puff rate of 80 ml per every two seconds for a total of 20 puffs. The entire inhaler device was weighed before and after the aerosol generation test to determine the amount of each sample that was released from the capsule. A preferred target amount released of at least 25 grams was established.

Sample A (mannitol based) released 30 grams. Sample B (myo-inositol based) released 34 grams. Sample C (erythritol based) released 30 grams. These samples all passed the target amount released target.

Sample D (adonitol based) released 9 grams. Sample E (xylitol based) released 14 grams. These samples did not pass the target amount released target.

The comparative sample "Comp Ex" (trehalose based) actually increased in weight by 0.1 grams, indicating that more water was absorbed than sample released.

While the adonitol and xylitol powders did not reach the target release value they still represented a significant improvement over the amorphous trehalose powder.

For the purpose of the present description and of the appended claims, except where otherwise indicated, all numbers expressing amounts, quantities, percentages, and so forth, are to be understood as being modified in all instances by the term "about." Also, all ranges include the maximum and minimum points disclosed and include any intermediate ranges therein, which may or may not be specifically enumerated herein. In this context, therefore, a number A is understood as A±2% of A. Within this context, a number A may be considered to include numerical values that are within general standard error for the measurement of the property that the number A modifies. The number A, in some instances as used in the appended claims, may deviate by the percentages enumerated above provided that the amount by which A deviates does not materially affect the basic and novel characteristic(s) of the claimed invention. Also, all ranges include the maximum and minimum points disclosed and include any intermediate ranges therein, which may or may not be specifically enumerated herein.

The invention claimed is:

1. An inhalable powder comprising:

crystalline dry powder particles comprising:

a solid salt of an alkaloid, wherein the salt of the alkaloid is solid at 25° C., wherein the solid salt of an alkaloid comprises nicotine bitartrate, nicotine aspartate, nicotine malate, or nicotine glutarate; and a sugar alcohol comprising erythritol, myo-inositol, adonitol, xylitol, or a combination thereof.

2. The inhalable powder claim 1, wherein the crystalline dry powder particles further comprise an amino acid.

3. The inhalable powder of claim 1, wherein the crystalline dry powder particles comprise sugar alcohol, amino acid and solid salt of an alkaloid, and at least selected crystalline dry powder particles each comprise a sugar alcohol matrix and the solid salt of an alkaloid dispersed within the sugar alcohol matrix.

4. The inhalable powder of claim 1, wherein the sugar alcohol is erythritol or myo-inositol.

5. The inhalable powder of claim 1, wherein the crystalline dry powder particles comprise about 60% wt. or greater sugar alcohol, and 10% wt. or greater amino acid and from about 1% to about 10% wt. solid salt of an alkaloid, and at least selected crystalline dry powder particles each comprise a sugar alcohol matrix and the solid salt of an alkaloid is dispersed within the sugar alcohol matrix.

6. The inhalable powder of claim 1, wherein the crystalline dry powder particles comprise erythritol or myo-inositol, and leucine, and nicotine bitartrate, and at least selected crystalline dry powder particles each comprise an erythritol or myo-inositol matrix and the nicotine bitartrate is dispersed within the erythritol or myo-inositol matrix.

7. The inhalable powder of claim 1, wherein the crystalline dry powder particles comprise erythritol or myo-inositol, and leucine, and nicotine aspartate, and at least selected crystalline dry powder particles each comprise an erythritol or myo-inositol matrix and the nicotine aspartate is dispersed within the erythritol or myo-inositol matrix.

8. The inhalable powder of claim 1, wherein the crystalline dry powder particles comprise erythritol or myo-inositol, and leucine, and nicotine glutarate, and at least selected crystalline dry powder particles each comprise an erythritol or myo-inositol matrix and the nicotine glutarate is dispersed within the erythritol or myo-inositol matrix.

9. The inhalable powder of claim 1, wherein the crystalline dry powder particles comprise erythritol or myo-inositol, and leucine, and nicotine malate, and at least selected crystalline dry powder particles each comprise an erythritol or myo-inositol matrix and the nicotine malate is dispersed within the erythritol or myo-inositol matrix.

10. The inhalable powder of claim 1, wherein the crystalline dry powder particles comprise 70% to 80% erythritol, and 15% to 25% wt. leucine and from about 1% to about 10% wt. nicotine bitartrate, nicotine aspartate, nicotine malate, or nicotine glutarate.

11. An inhalable powder system comprising a first population of crystalline dry powder particles of the powder of claim 1 and a second population of particles having a particle size greater than that of the first population of particles.

12. The inhalable powder system of claim 11, wherein the first population of crystalline dry powder particles has an MMAD particle size of from about 1 micrometre to about 5 micrometres and the second population of particles has an MMAD particle size of from 20 micrometres to 200 micrometres.

13. The inhalable powder of claim 1, wherein the crystalline dry powder particles comprise an amino acid coating the crystalline dry powder particles comprising the solid salt of an alkaloid dispersed within the crystalline sugar alcohol matrix.

14. The inhalable powder of claim 6, wherein the crystalline dry powder particles comprise 70% to 80% wt. erythritol or myo-inositol, and 15% to 25% wt. leucine and from about 1% to about 10% wt. nicotine bitartrate.

15. The inhalable powder of claim 9, wherein the crystalline dry powder particles comprise 70% to 80% wt. erythritol or myo-inositol, and 15% to 25% wt. leucine and from about 1% to about 10% wt. nicotine aspartate.

16. The inhalable powder of claim 8, wherein the crystalline dry powder particles comprise 70% to 80% wt. erythritol or myo-inositol, and 15% to 25% wt. leucine and from about 1% to about 10% wt. nicotine glutarate.

17. The inhalable powder of claim 9, wherein the crystalline dry powder particles comprise 70% to 80% wt. erythritol or myo-inositol, and 15% to 25% wt. leucine and from about 1% to about 10% wt. nicotine malate.

18. The inhalable powder of claim 1, wherein the crystalline dry powder particles comprise 70% to 80% myo-inositol, and 15% to 25% wt. leucine and from about 1% to about 10% wt. nicotine bitartrate, nicotine aspartate, nicotine malate, or nicotine glutarate.

* * * * *